US010961191B2

(12) United States Patent
Bodor et al.

(10) Patent No.: US 10,961,191 B2
(45) Date of Patent: *Mar. 30, 2021

(54) FORMULATION FOR SOFT ANTICHOLINERGIC ANALOGS

(71) Applicant: BODOR LABORATORIES, INC., Miami, FL (US)

(72) Inventors: Nicholas S. Bodor, Bal Harbour, FL (US); John J. Koleng, Austin, TX (US); David Angulo, Miami, FL (US)

(73) Assignee: BODOR LABORATORIES, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/683,792

(22) Filed: Nov. 14, 2019

(65) Prior Publication Data
US 2020/0113869 A1 Apr. 16, 2020

Related U.S. Application Data

(63) Continuation of application No. 15/125,039, filed as application No. PCT/US2015/020253 on Mar. 12, 2015, now abandoned, which is a continuation-in-part of application No. 14/285,488, filed on May 22, 2014, now abandoned.

(60) Provisional application No. 61/952,505, filed on Mar. 13, 2014.

(51) Int. Cl.
A61K 31/40 (2006.01)
C07D 207/12 (2006.01)
A61K 33/06 (2006.01)
A61K 47/10 (2017.01)
A61K 9/08 (2006.01)
A61K 9/00 (2006.01)
A61K 47/12 (2006.01)
A61K 47/34 (2017.01)
A61K 8/49 (2006.01)
A61K 9/06 (2006.01)
A61Q 15/00 (2006.01)
A61K 47/38 (2006.01)
A61K 47/24 (2006.01)

(52) U.S. Cl.
CPC .......... C07D 207/12 (2013.01); A61K 8/4913 (2013.01); A61K 9/0014 (2013.01); A61K 9/06 (2013.01); A61K 9/08 (2013.01); A61K 31/40 (2013.01); A61K 33/06 (2013.01); A61K 47/10 (2013.01); A61K 47/12 (2013.01); A61K 47/34 (2013.01); A61Q 15/00 (2013.01); A61K 47/24 (2013.01); A61K 47/38 (2013.01)

(58) Field of Classification Search
None
See application file for complete search history.

(56) References Cited

U.S. PATENT DOCUMENTS

| 5,232,689 | A | 8/1993 | Katsoulis et al. |
| 5,292,530 | A | 3/1994 | McCrea et al. |
| 6,433,003 | B1 | 8/2002 | Bobrove et al. |
| 7,399,861 | B2 | 7/2008 | Bodor |
| 7,417,147 | B2 | 8/2008 | Bodor |
| 7,538,219 | B2 | 5/2009 | Bodor |
| 7,576,210 | B2 | 8/2009 | Bodor |
| 8,071,639 | B2 | 12/2011 | Bodor |
| 8,147,809 | B2 | 4/2012 | Bodor |
| 8,153,669 | B2 | 4/2012 | Press |
| 8,383,625 | B2 | 2/2013 | Press |
| 8,568,699 | B2 | 10/2013 | Bodor |
| 8,618,160 | B2 | 12/2013 | Johnston et al. |
| 8,628,759 | B2 | 1/2014 | Bodor |
| 8,679,524 | B2 | 3/2014 | Wassenaar |
| 9,220,707 | B2 | 12/2015 | Bodor et al. |
| 9,744,105 | B2 | 8/2017 | Johnston et al. |
| 2003/0064040 | A1 | 4/2003 | Lukacsko |
| 2006/0088496 | A1 | 4/2006 | McManus et al. |
| 2006/0210504 | A1 | 9/2006 | Lukacsko |
| 2008/0234239 | A1 | 9/2008 | Wheeler et al. |
| 2009/0208437 | A1 | 8/2009 | Woehrmann et al. |
| 2009/0227590 | A1 | 9/2009 | Press et al. |
| 2009/0263341 | A1 | 10/2009 | Bodor |
| 2009/0291960 | A1 | 11/2009 | Press et al. |
| 2012/0237573 | A1 | 9/2012 | Wassenaar |
| 2015/0374621 | A1 | 12/2015 | Bodor |

FOREIGN PATENT DOCUMENTS

| CN | 101048126 A | 10/2007 |
| JP | 2001-523700 A | 11/2001 |
| JP | 2008-163010 A | 7/2008 |
| JP | 2009-515889 A | 4/2009 |
| WO | 99/26598 A1 | 6/1999 |
| WO | 2007/058971 A2 | 5/2007 |

(Continued)

OTHER PUBLICATIONS

Ji, F., Wu, W-M and Bodor, N., "Studies on a soft glycopyrrolate analog, SG-1" Pharmazie, 2002, pp. 138-141, 2-5, vol. 57, No. 2, Govi-Verlag, Germany.

(Continued)

Primary Examiner — James W Rogers
(74) Attorney, Agent, or Firm — Dentons US LLP

(57) ABSTRACT

Topical formulations comprising soft glycopyrrolates are useful for treating excessive sweating conditions in subjects, such as humans suffering from hyperhidrosis. Preferably, at least one soft anticholinergic agent is provided in an effective amount or concentration in an anhydrous formulation that can inhibit excessive perspiration resulting from a condition such as hyperhidrosis.

20 Claims, No Drawings

(56) References Cited

FOREIGN PATENT DOCUMENTS

| WO | 2009/051818 A1 | 4/2009 |
| WO | 2014/144075 A1 | 9/2014 |
| WO | 2015/138776 A1 | 9/2015 |

OTHER PUBLICATIONS

"Glycopyrronium bromide" downloaded at Wikipedia, http://en.wikipedia.org/wiki/Glycopyrronium_bromide on May 1, 2015.

Ji. F., et al., "Synthesis and Pharmacological Effects of New N-Substituted Soft Anticholinergics Based on Glycopyrrolate," J. Pharmacy and Pharmacology, vol. 57, No. 11, Nov. 1, 2005, pp. 1427-1435, John Wiley & Sons Ltd. London, GB (pub.).

Wu, W.M. et al. "Stereoisomers of N-Substituted Soft Anticholinergics and Zwitterion Metabolite Based on Glycopyrrolate—Syntheses and Pharmacological Evaluations," Die Pharmazie, Mar. 2008, vol. 63, No. 3, pp. 200-209.

Kirk et al., "Esterification and Esters, Organic", Kirk-Othmer Encyclopedia of Chemical Technology, 4th ed., Feb. 1994, vol. 9, ISBN-10 0471526770. http://vigoschools.org/-mmc3/AP%20Lab/ap%02lab%20documents/Esterification.pdf; p. 24, para 8.

International Search Report and Written Opinion dated Jul. 17, 2014 for International Application No. PCT/US2014/028332, 12 pages.

Office Action dated Sep. 17, 2014 for parent U.S. Appl. No. 14/285,488.

Office Action dated Jan. 22, 2015 for parent U.S. Appl. No. 14/285,488.

Office Action dated Feb. 4, 2015 for related U.S. Appl. No. 14/213,242.

International Search Report dated Jun. 18, 2015 for corresponding International Application No. PCT/US2015/020253, 2 pages.

Written Opinion of the International Searching Authority dated Jun. 18 for corresponding International Application No. PCT/US2015/020253, 5 pages.

European Office Action dated Oct. 6, 2017 in corresponding European Patent Application No. 15762178.0, 8 pages.

Japanese Office Action dated Oct. 4, 2017 in corresponding Japanese Patent Application No. 2016-556899, 7 pages.

Chinese Office Action dated Aug. 2, 2018 in corresponding Chinese Patent Application No. 201580013622.0, 21 pages.

Extended European Search Report dated Oct. 6, 2017 in corresponding European Patent Application No. 15762178.0, 8 pages.

Raj Sakamuri, "Esters, Organic", Kirk-Othmer Encyclopedia of Chemical Technology, John Wiley & Sons, Inc., vol. 10, pp. 497-526 (Dec. 19, 2003).

Indonesian Office Action dated Sep. 24, 2019 in corresponding Indonesian Patent Application No. P00201605975 (with English translation), 4 pages.

Vietnamese Office Action dated Oct. 21, 2019 in corresponding Vietnamese Patent Application No. 1-2016-03285 (with English translation), 3 pages.

Examination Report dated Sep. 1, 2020 in Australian Patent Application No. 2016297601, 4 pages.

Examination Report in European Patent Office in Application No. 17831882.0, dated Nov. 23, 2020.

Lachenmeier, Dirk W., "Safety evaluation of topical applications of ethanol on the skin and inside the oral cavity", Journal of Occupational Medicine and Toxicology, vol. 3, No. 26, 16 pages (Nov. 13, 2008).

FORMULATION FOR SOFT ANTICHOLINERGIC ANALOGS

CROSS-REFERENCE TO EARLIER APPLICATIONS

This application is a continuation of U.S. application Ser. No. 15/125,039, filed Sep. 9, 2016, which is a U.S. National Stage of International Application No. PCT/US2015/02053, filed Mar. 12, 2015, which is a continuation-in-part of U.S. application Ser. No. 14/285,488, filed May 22, 2014, now abandoned, which claims priority to U.S. Provisional Application 61/952,505, filed Mar. 3, 2014, each hereby expressly incorporated by reference in its entirety and each assigned to the assignee hereof.

BACKGROUND

Various anticholinergic compounds and formulations for those compounds have been previously described. Glycopyrrolate is among the quaternary ammonium anticholinergics which have reduced CNS-related side effects as they cannot cross the blood-brain barrier; however, because glycopyrrolate is eliminated mainly as unchanged drug or active metabolite, its topical administration is often associated with common undesirable anticholinergic systemic side effects. To increase the therapeutic index of anticholinergics, the soft drug approach has been applied in a number of different designs starting from various lead compounds.

Soft anticholinergic zwitterions have been described in U.S. Pat. No. 8,568,699, and its related patents, U.S. Pat. Nos. 8,071,639; 7,538,219; and 7,417,147. Soft anticholinergic esters have been described in U.S. Pat. No. 8,628,759 and its related U.S. Pat. Nos. 8,147,809; 7,576,210; and 7,399,861. Each of the U.S. Pat. Nos. 8,568,699 and 8,628,759 and their related patents, U.S. Pat. Nos. 8,147,809; 8,071,639; 7,576,210; 7,538,219; 7,417,147; and 7,399,861 are hereby incorporated by reference in their entirety.

Recently, it has been discovered that soft anticholinergic analogs may be applied topically in treating hyperhidrosis. Hyperhidrosis is an idiopathic pathological condition characterized by excessive, uncontrollable sweating beyond that required to cool the body. Hyperfunction of the sweat glands and disturbance of their cholinergic stimulation have been described as possible causes of this condition.

Hyperhidrosis most often involves one or several anatomic areas, especially the hands, axillae, feet or face, although it can even involve the whole body. Axillary hyperhidrosis is the most common form, followed by palmar hyperhidrosis. Aluminum and other polycationic-based antiperspirants alone are generally not effective in treating this excessive perspiration. Oral medications are occasionally beneficial, but may have side effects.

Other therapeutic alternatives include botulinum toxin injection, iontophoresis and surgical procedures such as endoscopic thoracic sympathectomy. Botulinin toxin injections are painful, expensive and need to be repeated every 6 months to achieve the desired benefit. Iontophoresis has limited efficacy and cannot be used for axillary areas and although the surgery affords permanent benefit in some 40% to 90% of affected individuals, it is invasive, requires general anesthesia and is not without potential side effects. As many as 50% of persons who have undergone thoracic sympathectomy develop compensatory and annoying sweating of the trunk or thighs.

A non-invasive, convenient and effective treatment having high sweat reduction activity, long duration, and with fewer side effects would be a welcome alternative for treating hyperhidrosis. Topical formulations comprising soft anticholinergic analogs, such as esters of glycopyrrolate, have been proposed for use in treating hyperhidrosis; however, stable, pharmaceutically acceptable formulations which can meet regulatory requirements or provide commercially viable shelf-life for such products have been elusive. Thus, what is needed in the art is a stable, pharmaceutically acceptable, and commercially viable formulation for a topically administered composition comprising a soft anticholinergic analog.

SUMMARY

The subject invention concerns topical formulations for treating excessive sweating conditions in subjects, such as humans suffering from hyperhidrosis. Preferably, a composition of the invention comprises at least one soft anticholinergic agent in an effective amount or concentration that can inhibit excessive perspiration resulting from a condition such as hyperhidrosis. For example, one preferred embodiment of the invention is a topical composition comprising at least one of a compound having the formula (1):

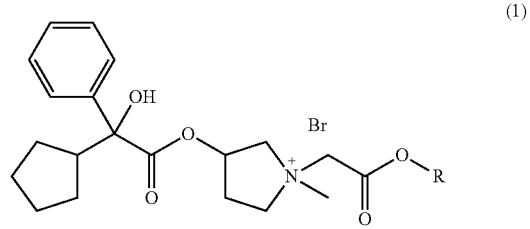

wherein, R is methyl or ethyl, said compound having the R, S, or RS steroisomeric configuration at the 2 position and 1' and 3' position, or being a mixture thereof.

One preferred embodiment of a topical composition of the invention comprises at least one of a compound having the following stereospecific formula (2):

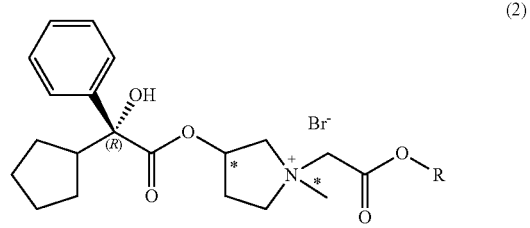

wherein, R is methyl or ethyl, said compound having the R stereoisomeric configuration at the 2 position and having R, S, or RS steroisomeric configuration at the 1' and 3' position (designated by asterisks), or being a mixture thereof.

The subject invention further includes a topical pharmaceutical composition comprising one or more of the compounds of the foregoing formula, and one or more pharmaceutically acceptable carrier or excipient. A composition of the invention can further comprise one or more of the compounds of the foregoing formula and, optionally, another active agent, such as an antiperspirant, e.g., aluminum chloride.

Methods of treating or inhibiting or ameliorating excessive sweating, including conditions such as hyperhidrosis, using a topical composition as described herein, are also included as part of this invention.

A composition of the subject invention can be formulated as a solid or semi-solid, powder, gel, cream, lotion, foam, solution, suspension, aerosol, patch, wipes or emulsion, or the like, and is preferably formulated for topical application for the treatment, prevention, or amelioration of hyperhidrosis. More preferably, a composition of the invention is formulated as an anhydrous topical gel, which can provide certain advantages, including superior stability or increased shelf-life for the composition, as well as the benefit of minimizing or eliminating the need for a separate preservative in the composition.

Additional advantages for a topical anhydrous gel composition of the invention include properties such fast drying time, limited residue on the skin or clothing, and facilitation of a capability to be dispensed in metered amounts of product per application. A formulation of the invention can further mask stickiness properties that some soft-anticholinergics, such as certain compounds described herein, may have.

One preferred formulation comprises about 0.1% to about 30% of the compound in 70-99.9% of a non-aqueous solvent, such as an alcohol, e.g., ethanol, isopropanol, methanol, or the like. The formulation of the invention can further include one or more additional excipient, including a gelling or viscosity controlling excipient, which can, itself, be anhydrous or non-aqueous.

A method for treating, preventing, or ameliorating hyperhidrosis in a subject can comprise:

a) providing a topical, anhydrous composition comprising a pharmaceutically acceptable vehicle and from about 0.1% to about 30% of a compound having the formula (1):

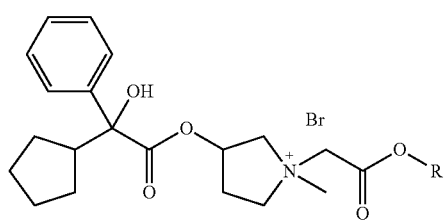

(1)

wherein R is methyl or ethyl; and b) topically administering the composition to a subject suffering from excessive sweating, such as hyperhidrosis.

Another embodiment of a method for treating, preventing, or ameliorating hyperhidrosis in a subject can comprise:

a) providing a topical, anhydrous composition comprising a pharmaceutically acceptable vehicle and from about 0.1% to about 30% of a compound having the formula (2):

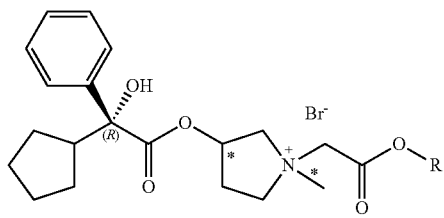

(2)

wherein R is methyl or ethyl, said compound having the R stereoisomeric configuration at the 2 position and the R, S, or RS steroisomeric configuration at the 1' and 3' position, or being a mixture thereof; and b) topically administering the composition to a subject suffering from excessive sweating, such as hyperhidrosis.

Advantageously, the method can provide reduction of excessive sweating for up to about 48 hours. Moreover, surprisingly, topical administration of the composition can unexpectedly provide a reduction in sweat production, as compared to baseline conditions, for at least about six (6) hours by an amount which is substantially equivalent to the reduction of sweat production resulting from administration of a composition comprising an equivalent concentration of glycopyrrolate, also compared to baseline conditions. Soft ester analogues of glycopyrrolate were previously believed to require up to 5-10 times the concentration of glycopyrrolate to provide substantially equivalent activity.

A method of the invention is preferably carried out by administration of the composition to a human subject, applied topically, to the skin of the subject at a superficial anatomic area in need of sweat reduction. Preferably, the anatomic area for application or administration of the composition is selected from a hand palm area, a foot plantar area, a groin area, an axilla area, and facial area of the subject.

The subject method can reduce sweat production by about 25% to about 99%, preferably by about 30% to about 90%, more preferably by at least 50%, which can be a clinically significant endpoint for an indication for treating hyperhidrosis.

As previously described, the method can employ the composition formulated as a solid or semi-solid, powder, gel, cream, lotion, foam, solution, suspension, aerosol, patch, wipes or emulsion, or the like and preferably comprises about 0.1% to about 30% concentration of the compound, more preferably about 1% to about 20% concentration of the compound, and most preferably about 2% to about 10% concentration of the compound.

A method in accordance with the subject invention can comprise topically administering to a subject as needed (prn), a composition of the invention. Administrations are preferably at least one time per week, more preferably at least three to four times per week (e.g., every other day), or can be administered more frequently such as once-daily (QD), for example, before bedtime (typically, at night) or after the subject awakens (typically in the morning, and preferably after a bath or shower); twice-daily (BID), e.g., every 10-12 hours; thrice-daily (TID), e.g., every 6-9 hours; four times-daily (QID), e.g., every 3-5 hours; with a preferred upper limit of about 6-8 doses or applications per day.

Surprisingly, the subject method, after single or multiple applications can reduce sweat production for a period of about 4 hours to about 24 hours, and preferably for a period of about 6 hours to about 12 hours.

A preferred composition of the invention comprises:

One or more soft glycopyrrolate analogues as an active ingredient; and

One or more non-aqueous solvent.

As described herein, a formulation of the subject invention is preferably a gel. Accordingly a more preferred composition comprises:

One or more soft glycopyrrolate analogues as an active ingredient;

One or more non-aqueous, pharmaceutically acceptable solvents; and

One or more gelling or viscosity controlling agents.

Preferably, the soft glycopyrrolate analogue is a soft anticholinergic ester. A preferred non-aqueous solvent can be a low molecular weight alcohol, such as methanol, ethanol or isopropanol.

Advantageously, an alcohol solvent can provide for a self-preserving composition, which can provide microbial stability to the composition without added preservatives.

Alcohols and other ingredients can also inhibit bacterial growth and provide deodorant properties to the composition.

A further advantage of a composition according to the subject invention can be provided by a non-aqueous solvent which is volatile, especially at localized temperatures generated by body heat so that, when topically applied to a subject, provides a rapidly drying composition.

A preferred gelling or viscosity controlling agent can be a modified cellulose, e.g., hydroxypropyl cellulose (HPC), such as the commercially available Klucel®, which can preferably provide viscosity of the composition of about 100 to about 10,000 cps.

DETAILED DESCRIPTION

Throughout this specification, the following definitions, general statements and illustrations are applicable:

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compounds or compositions described herein, i.e., the process or composition is limited to the specified steps or materials and those which do not materially affect the basic and novel characteristics of the invention.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the recitation of a numerical range for a variable is intended to convey that the variable can be equal to any values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's The Pharmacological Basis of Therapeutics, 10th Ed., McGraw Hill Companies Inc., New York (2001).

As used herein, "treating" means reducing, hindering or inhibiting the development of, controlling, inhibiting, alleviating and/or reversing the symptoms in the individual to which a composition comprising a compound of the invention has been administered, as compared to the symptoms of an individual not being administered the compound or composition. A practitioner will appreciate that the combinations, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The subject compounds or compositions can also prevent the symptoms, or prevent the occurrence of the symptoms in the individual to which a composition comprising a compound of the invention has been administered, as compared to the symptoms of an individual not being administered the compound or composition.

The methods described herein are intended for use with any subject/patient that may experience their benefits. Thus, the terms "subjects" as well as "patients," "individuals" and "warm-blooded animals" include humans as well as non-human subjects, such as animals that may experience excessive sweating.

Compounds useful in a composition of the invention include those of the formula (1):

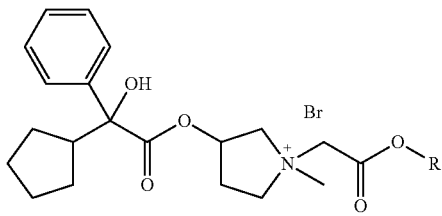

(1)

wherein R is methyl or ethyl.

The compound can have R, S, or RS steroisomeric configuration at the 2 position and at the 1' and 3' positions, or being a mixture thereof.

Compounds of the invention having the R configuration with respect to chiral center 2 are of particular interest. For example, a preferred compound useful in a composition of the invention has the stereospecific formula (2):

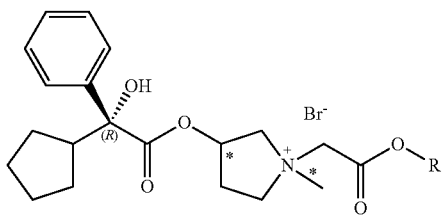

(2)

wherein R is methyl or ethyl, said compound having the R stereoisomeric configuration at the 2 position and the R, S, or RS stereoisomeric configuration at the 1' and 3' positions (designated by asterisks), or being a mixture thereof.

The following compounds are of particular interest for use in a composition of the invention:
(i) 3-[2-cyclopentylphenylhydroxyacetoxy]-1'-methyl-1'-methoxycarbonylmethyl-pyrrolidinium bromide;
(ii) 3-[2-cyclopentylphenylhydroxyacetoxy]-1'-methyl-1'-ethoxycarbonylmethyl-pyrrolidinium bromide;
(iii) 3-[2(R)-cyclopentylphenylhydrmyacetoxy]-1'-methyl-1'-methoxycarbonylmethyl-pyrrolidinium bromide;
(iv) 3-[2(R)-cyclopentylphenylhydroxyacetoxy]-1'-methyl-1'-ethoxycarbonylmethyl-pyrrolidinium bromide;
(v) 3'(R)-[2(R)-cyclopentylphenylhydroxyacetoxy]-1'-methyl-1'-methoxycarbonylmethyl-pyrrolidinium bromide;
(vi) 3'(S)-[2(R)-cyclopentylphenylhydroxyacetoxy]-1'-methyl-1'-methoxycarbonylmethyl-pyrrolidinium bromide;
(vii) 3'(R)-[2(R)-cyclopentylphenylhydroxyacetoxy]-1'-methyl-1'-ethoxycarbonylmethyl-pyrrolidinium bromide;
(viii) 3'(S)-[2(R)-cyclopentylphenylhydroxyacetoxy]-1'-methyl-1'-ethoxycarbonylmethyl-pyrrolidinium bromide;
(ix) 1'(R)-3'(R)-[2(R)-cyclopentylphenylhydroxyacetoxy]-1'-methyl-1'-ethoxycarbonylmethyl-pyrrolidinium bromide;
(x) 1'(R)-3'(S)-[2(R)-cyclopentylphenylhydroxyacetoxy]-1'-methyl-1'-ethoxycarbonylmethyl-pyrrolidinium bromide;
(xi) 1'(S)-3'(R)-[2(R)-cyclopentylphenylhydroxyacetoxy]-1'-methyl-1'-ethoxycarbonylmethyl-pyrrolidinium bromide;
(xii) 1'(S)-3'(R)-[2(R)-cyclopentylphenylhydroxyacetoxy]-1'-methyl-1'-ethoxycarbonylmethyl-pyrrolidinium bromide;
(xiii) 1'(R)-3'(R)-[2(R)-cyclopentylphenylhydroxyacetoxy]-1'-methyl-1'-methoxycarbonylmethyl-pyrrolidinium bromide;
(xiv) 1'(R)-3'(S)-[2(R)-cyclopentylphenylhydroxyacetoxy]-1'-methyl-1'-methoxycarbonylmethyl-pyrrolidinium bromide;
(xv) 1'(S)-3'(R)-[2(R)-cyclopentylphenylhydroxyacetoxy]-1'-methyl-1'-methoxycarbonylmethyl-pyrrolidinium bromide; and
(xvi) 1'(S)-3'(R)-[2(R)-cyclopentylphenylhydroxyacetoxy]-1'-methyl-1'-methoxycarbonylmethyl-pyrrolidinium bromide.

It is noted that the above compounds are identical to those originally disclosed with a correct, but different, naming scheme, in U.S. Provisional Patent Application, Ser. No. 61/952,505. The compounds were previously and respectively disclosed as:
(i) 3-(2-cyclopentylphenylhydroxyacetoxy]-1'-methyl-1'-methoxycarbonylmethyl-pyrrolidinium bromide;
(ii) 3-(2-cyclopentylphenylhydroxyacetoxy]-1'-methyl-1'-ethoxycarbonylmethyl-pyrrolidinium bromide;
(iii) (2R) 3-(2-cyclopentylphenylhydroxyacetoxy]-1'-methyl-1'-methoxycarbonylmethyl-pyrrolidinium bromide;
(iv) (2R) 3-(2-cyclopentylphenylhydroxyacetoxy]-1'-methyl-1'-ethoxycarbonylmethyl-pyrrolidinium bromide;
(v) (2R,3'R) 3-(2-cyclopentylphenylhydroxyacetoxy]-1'-methyl-1'-methoxycarbonylmethyl-pyrrolidinium bromide;
(vi) (2R,3'S) 3-(2-cyclopentylphenylhydroxyacetoxy]-1'-methyl-1'-methoxycarbonylmethyl-pyrrolidinium bromide;
(vii) 3'(R)-[2(R)-cyclopentylphenylhydroxyacetoxy]-1'-methyl-1'-ethoxycarbonylmethyl-pyrrolidinium bromide;
(viii) (2R,3'S) 3-(2-cyclopentylphenylhydroxyacetoxy]-1'-methyl-1'-ethoxycarbonylmethyl-pyrrolidinium bromide;
(ix) (2R,1'R,3'S) 3-(2-cyclopentylphenylhydroxyacetoxy]-1'-methyl-1'-ethoxycarbonylmethyl-pyrrolidinium bromide;
(x) (2R,1'S,3'S) 3-(2-cyclopentylphenylhydroxyacetoxy]-1'-methyl-1'-ethoxycarbonylmethyl-pyrrolidinium bromide;
(xi) (2R,1'R,3'R) 3-(2-cyclopentylphenylhydroxyacetoxy]-1'-methyl-1'-ethoxycarbonylmethyl-pyrrolidinium bromide;
(xii) (2R,1'S,3'R) 3-(2-cyclopentylphenylhydroxyacetoxy]-1'-methyl-1'-ethoxycarbonylmethyl-pyrrolidinium bromide;
(xiii) (2R,1'R,3'S) 3-(2-cyclopentylphenylhydroxyacetoxy]-1'-methyl-1'-methoxycarbonylmethyl-pyrrolidinium bromide;

(xiv) (2R,1'S,3'S) 3-(2-cyclopentylphenylhydroxyacetoxy]-1'-methyl-1'-methoxycarbonylmethyl-pyrrolidinium bromide;

(xv) (2R,1'R,3'R) 3-(2-cyclopentylphenylhydroxyacetoxy]-1'-methyl-1'-methoxycarbonylmethyl-pyrrolidinium bromide; and (xvi) (2R,1'S,3'R) 3-(2-cyclopentylphenylhydroxyacetoxy]-1'-methyl-1'-methoxycarbonylmethyl-pyrrolidinium bromide.

The above compounds (i)-(xvi) can be used alone or two or more of the above compounds can be used in combination in a single composition. Various methods of making the instant compounds are described in the art.

An anticholinergically effective amount of such an agent inhibits the effect of acetylcholine by blocking its binding to muscarinic cholinergic receptors at neuroeffector sites. Subjects in need of a method of eliciting an anticholinergic response are those suffering from conditions which respond to treatment with an anticholinergic agent, including subjects suffering from excessive sweating or hyperhidrosis.

A compound included in a composition of the invention may be used on its own or combined with other inactive or active substances according to the invention. These include, in particular, antiperspirant active substances such as aluminum chloride, aluminum chlorhydrate, or the like.

Whether or not the compound of the invention is used in conjunction with other active substances, it is typically administered in the form of a pharmaceutical composition comprising an anticholinergically effective amount of the compound and a non-toxic pharmaceutically acceptable carrier therefor. Pharmaceutically acceptable carriers, or diluents, are well-known in the art. The carriers may be any inert material, organic or inorganic, powders, liquid, or gases suitable for administration, such as: alcohols, gelatin, gum arabic, lactose, microcrystalline cellulose, starch, sodium starch glycolate, calcium hydrogen phosphate, magnesium stearate, talcum, colloidal silicon dioxide, and the like.

Surprisingly, it has been discovered that preferred formulations, having advantageous properties, result when no water or aqueous carrier is added to the formulation. Thus, a preferred composition of the subject invention is an anhydrous formulation. By the term "anhydrous", is meant that no water or aqueous excipient is added in the formulation. Analysis of the final formulation may identify the presence of water, due to hygroscopicity of the one or more active compounds or one or more excipients, the presence of a hydrate form of one or more ingredients in the formulation, or other inherent presence of water. However, because no water or aqueous excipient, carrier, or other component is specifically added, a formulation of the subject invention is considered and understood to be "anhydrous."

Thus, having no free or unbound water added, a composition of the invention is therefore "substantially free of water" and is substantially free of aqueous excipients, though hydrated forms of ingredients, such as aluminum chlorhydrate used as an antiperspirant, may be included in such anhydrous formulation.

Such compositions may also contain other pharmaceutically active agents, as noted above, and/or conventional additives such as solvents, stabilizers, wetting agents, emulsifiers, buffers, binders, disintegrants, fragrances, lubricants, glidants, antiadherents, propellants, and the like.

The carrier, e.g., non-active ingredient, can be or comprise a solvent, e.g., an alcohol, such as ethanol, isopropanol, or the like, in which the compound is soluble or at least slightly soluble. It is preferred that the apparent pH of the composition be acidic (i.e. apparent pH<7). Where the compound is slightly, moderately, or highly water-insoluble, non-toxic, pharmaceutically acceptable organic solvents or co-solvents can be used. For example, an alcohol, such as isopropyl alcohol, ethanol, or the like can be used alone or as a cosolvent with another non-aqueous solvent.

The novel composition of the invention can be formulated as a solid, semi-solid, or liquid form, such as powders, solutions, lotions, creams, gels, semi-solid sticks, foams, sprays, aerosols, solutions, suspensions or emulsions, patches, wipes and the like, and is preferably formulated for topical administration. By way of illustration only, for treating hyperhydrosis, a topical preparation formulated as an anhydrous antiperspirant stick, gel, spray, cream, solution, foam, emulsion or the like can be preferred.

Alternatively, a composition of the invention may be administered in the form of liposome or micelle delivery systems, such as small unilamellar vesicles, large unilamellar vesicles and multilamellar vesicles. Liposomes can be formed from a variety of phospholipids, such as cholesterol, stearylamine or phosphatidylcholines.

In preparing a formulation, it may be necessary to mill the active compound to provide the appropriate particle size prior to combining with the other ingredients. If the active compound is substantially insoluble, it ordinarily is milled to a particle size of less than 200 mesh.

Some examples of suitable topical excipients include alcohols, aloe vera gel, hexylene glycol, propylene glycol, dimethicone, PGE, allantoin, glycerin, vitamin A and E oils, mineral oil, PPG2, myristyl propionate lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, and methyl cellulose.

The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, modified, sustained or delayed release or activity of the active ingredient after administration and/or application to the subject by employing procedures known in the art.

The composition may additionally contain one or more optional additives such as colorants, perfumes, or the like. In practice, each of these optional additives should be compatible with the active compound. Compatible additives are those that do not prevent the use of or result in the degradation of the compound in the manner described herein.

Other suitable formulations for use in the present invention can be found in publications such as Remington's Pharmaceutical Sciences.

For purposes of illustration, liquid formulation dosages are expressed based on a percent solution (g/100 ml) or percent concentration (w/v) unless otherwise stated. For solid formulation dosages, the percent concentration can be expressed as mg/mg, or w/w concentrations unless otherwise stated. A person of ordinary skill in the art would readily understand the percent concentration in the context of the type of formulation described.

In general, a therapeutically effective or anticholinergically effective amount of a compound of the invention is from about 0.1% solution (1 mg/ml) to about 100% solution (1,000 mg/ml). Preferably, the topical composition dose is from about 0.1% concentration to about 30% concentration, and is most preferred using a dose application volume of approximately 0.5 to about 1.0 ml of a composition comprising about 3% to about 6%, e.g., about 5%, of the compound per treated area.

The exact dosage of a compound of the invention can vary depending on its potency, the mode of administration, the application area, the age and weight of the subject and the severity of the condition to be treated. The daily dosage may be administered singly or multiply one to four times daily or more.

Administration prior to bedtime does not imply at night or a particular hour or time of day; rather, before or prior to bedtime means that the composition is preferably administered, generally within about 1-2 hours prior to a person's normal rest or sleep (typically 4 to 10-hour) period. A before bedtime administration time can provide a preferred response or activity of the active compounds of the invention.

Administration of a composition of the invention can provide a substantially identical or similar clinical (sweat reduction) response in a subject, as compared to administration of a composition containing the same concentration of glycopyrrolate. Thus, the results of this discovery are surprising in view of previously published mydriatic studies which suggested that the subject compounds in a composition were required to be present in concentration from 5 times to 10 times the concentration of a glycopyrrolate composition exhibiting a similar or substantially identical clinical response.

In addition, administration of a second dose within about 6-10 hours following the initial dose can also be a preferred method of administration or dosing regimen.

The topical composition for treating hyperhidrosis can be a liquid solution, semi-solid, or solid. Solutions are prepared in the usual way, e.g. with the addition of excipients, and can include preservatives such as p-hydroxybenzoates, or stabilizers such as alkali metal salts of ethylenediamine tetraacetic acid, optionally using emulsifiers and/or dispersants, and organic solvents may optionally be used as solvating agents or dissolving aids, and transferred into vials, ampules, bottles, tubes, syringes, or the like.

However, the anhydrous composition of the invention can have the advantage of minimizing, or eliminating, the need for an additional preservative to be included in the formulation. Thus, one preferred embodiment of a composition of the invention is a substantially "preservative-free" composition. By "preservative-free" is meant that the composition, though containing an alcohol or other organic solvent which may provide some preserving properties, no additional preservative component, added specifically for its preservative property, is added to the composition.

Additional excipients may be used in a composition of the invention, including, for example, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulfite liquors, methylcellulose, starch and polyvinylpyrrolidone) and lubricants (e.g. magnesium stearate, talc, stearic acid and sodium lauryl sulphate).

Compositions of the invention can be formulated using known techniques, and are generally accepted as being formulated with commonly known excipients, including preservatives if needed. For example, the patent literature describes that soft glycopyrrolate compounds are water-soluble, or at least partially water-soluble. Accordingly, soft glycopyrrolates compounds, such as soft anticholinergic analogs (e.g., esters) were earlier described as capable of being be formulated in buffer (aqueous or water-based) solutions. However, this invention concerns the discovery that aqueous components added to the formulation can increase the impurities found in the composition, can decrease the stability of the active compound, and can consequently decrease the shelf-life of the product compared to anhydrous formulations comprising a soft anticholinergic analogue as an active ingredient.

Moreover, decreased stability and increased impurities found for a soft anticholinergic analog formulated in an aqueous or water-based composition would suggest or even require an added preservative to be included in the composition.

In addition to the general preference or need to decrease exposure to preservative chemicals by the subject being treated, certain preservatives, such as the antioxidant, ascorbic acid, can have additional disadvantages when topically applied in an aqueous preparation. For example, an aqueous preparation comprising ascorbic acid was found to produce a pink-colored residue on the skin of individuals after a few to several hours following exposure to the preparation.

A preservative-free composition, such as an ascorbic acid-free composition, can therefore provide a further advantage of maintaining a colorless preparation following application and during residence on the skin of a subject. A composition comprising citric acid did not result in a pink colored residue following application of the composition to the skin; therefore a composition of the invention can include citric acid as an antioxidant.

The following experimental data demonstrate that aqueous or water-based compositions result in the presence of increased impurities identified in the composition, and decreased stability of the composition, which can lead to reduced shelf-life for a product comprising the composition. Adequate shelf-life can be an advantageous factor for regulatory approval, as well as commercial success for a topical gel composition.

The experimental data presented below also demonstrate the reduction of impurities identified, and increased stability for a product comprising an anhydrous topical gel in accordance with the subject invention.

Example 1—Aqueous Formulations

Aqueous, or water-based, topical formulations are the most common in view of the availability of gel-forming components which interact with water to form hydrogels. The following examples were conducted using the compound, 3'(R)-[2(R)-cyclopentylphenylhydroxyacetoxy]-1'-methyl-1'-ethoxycarbonylmethyl-pyrrolidinium bromide, (compound (vii) in the above list), which is designated as "BBI-4000" for convenience of reference.

The following Table I shows the components included in an aqueous formulations comprising BBI-4000, a soft anticholinergic ester, prepared and subjected to impurity and stability testing:

TABLE I

| Material | BB-61-1 | BB-62-1 | BB-63-1 | BB-64-1 | BB-65-1 |
|---|---|---|---|---|---|
| | Lot Number (% w/w) | | | | |
| BBI-4000 | 2.00 | 2.00 | 2.00 | 2.00 | 2.00 |
| Hydroxyethyl Cellulose | 1.00 | 1.00 | 1.00 | 1.00 | 1.00 |
| Hexylene Glycol | 5.00 | 5.00 | 5.00 | 5.00 | 5.00 |
| Benzyl Alcohol | 1.00 | 1.00 | 1.00 | 1.00 | 1.00 |
| Ethanol 95% | 26.31 | 26.32 | 26.32 | 26.32 | 26.32 |
| Polysorbate 80 | 1.00 | 1.00 | 1.00 | 1.00 | 1.00 |
| Dimethiconol Blend 20 | 2.50 | 2.50 | 2.50 | 2.50 | 2.50 |
| Dibasic Sodium Phosphate, Dried | | 0.09 | 0.09 | 0.09 | |
| Monobasic Sodium Phosphate, Anhydrous | | 0.53 | 0.53 | 0.53 | |
| Citric Acid, Anhydrous | | | | | 0.20 |
| Trisodium Citrate Dihydrate | | | | | 1.16 |
| Water | 61.19 | 60.56 | 60.56 | 60.56 | 59.83 |
| 2N HCL | to pH 5 | to pH 4.5 | to pH 5 | to pH 5.5 | to pH 5 |
| 2N NaOH | to pH 5 | to pH 4.5 | to pH 5 | to pH 5.5 | to pH 5 |

An HPLC method was developed at a commercial laboratory for assaying the soft anticholinergic analogue, and related substances (impurities):

Apparatus:
High performance liquid chromatography (HPLC) system
Chromatography data system
XBridge Shield RP18, 4.6×150 mm, 3.5 µm HPLC column
Analytical balance capable of weighing to 0.00001 g
Ultrasonic bath
Volumetric flasks, 1, 5 mL
Syringe Filter: 25 mm, 0.45 µm, HPF Millex-HV, Millipore or suitable alternative
Reagents, Supplies, Media and Solutions:
BBI-4000 standard
Water, HPLC grade
Acetonitrile (can), Optima grade
Trifluroacetic acid (TFA), Fisher
Mobile Phase "A": 0.1% TFA in Water
Mobile Phase "B": 0.1% TFA in Acetonitrile
Auto Sampler Flush: 1:1 Water:Acetonitrile
Diluent: Acetonitrile BBI-4000 Standard Preparation (2 mg/mL in Diluent):
The standards were prepared in duplicate by weighing 2.0±0.1 mg of BBI-4000 into 1 mL volumetric flasks. Dissolved and diluted to volume with acetonitrile and mixed by inversion.

Sample Preparation (BBI-4000 Gels):
Gel samples were prepared in duplicate at a target concentration of 2 mg/mL in a 5-mL volumetric flask. Added 1.5 ml H$_2$O and mixed to disperse the sample. Diluted to volume with acetonitrile and filtered an aliquot through a syringe filter.

HPLC Conditions:
The liquid chromatographic system was set-up as follows:
HPLC Column: XBridge Shield RP18, 4.6×150 mm, 3.5 µm
Column Temp.: 25±1° C.
Sample Temp.: ambient
Flow Rate: 1.5 mL/min
Injection Volume: 104
UV Detection: 220 nm
Run Time: 20 minutes The assay was conducted on formulations at differing pH values, and the results are shown in Table II, below, for "Time-Zero" and at 7 days at 40° C.:

TABLE II

HPLC Assay and Impurities by HPLC at Time Zero:

| | | un-buffered | Phosphate pH 4.5 | Phosphate pH 5.0 | Phosphate pH 5.5 | Citrate pH 5.0 |
|---|---|---|---|---|---|---|
| | | Sample Description | | | | |
| | | Lot number | | | | |
| | | BB-61-1 | BB-62-1 | BB-63-1 | BB-64-1 | BB-65-1 |
| BBI-4000 | Assay (Wt %) | 1.68% | 2.08% | 1.84% | 2.13% | 2.10% |
| | TAN % | 59.27% | 80.36% | 73.48% | 84.68% | 82.24% |
| Impurities (area %) | RRT 0.15 | 13.22% | 13.35% | 13.71% | 13.67% | 13.33% |
| | RRT 0.16 | — | — | — | — | 2.98% |
| | RRT 0.76 | 16.41% | 2.27% | 7.09% | 0.11% | 0.38% |
| | RRT 0.81 | 9.11% | 2.28% | 4.43% | 0.74% | 0.34% |
| | RRT 1.05 | 0.12% | — | — | — | — |
| | RRT 1.08 | 0.32% | 0.77% | 0.49% | 0.71% | 0.70% |
| | RRT 1.26 | 0.19% | 0.21% | 0.14% | — | — |
| | RRT 1.27 | 1.11% | 0.12% | 0.59% | — | — |
| | RRT 1.45 | — | 0.57% | — | — | — |
| | RRT 1.51 | 0.06% | 0.07% | 0.07% | 0.09% | 0.06% |
| | RRT 1.87 | 0.19% | — | — | — | — |
| Total Impurities | | 40.73% | 19.64% | 26.52% | 15.32% | 17.76% |

TABLE II

HPLC Assay and Impurities by HPLC at 7-Days

| | | Sample Description | | | | |
|---|---|---|---|---|---|---|
| | | un-buffered | Phosphate pH 4.5 | Phosphate pH 5.0 | Phosphate pH 5.5 | Citrate pH 5.0 |
| | | | | Lot number | | |
| | | BB-61-1 | BB-62-1 | BB-63-1 | BB-64-1 | BB-65-1 |
| BBI-4000 | Assay (Wt %) | 1.44% | 1.90% | 1.70% | 1.91% | 1.85% |
| | TAN % | 63.52% | 84.14% | 73.51% | 85.60% | 84.61% |
| Impurities (area %) | RRT 0.13 | 4.78% | 4.93% | 5.00% | 4.90% | 5.12% |
| | RRT 0.80 | 18.93% | 5.78% | 11.14% | 4.65% | 5.11% |
| | RRT 0.84 | 10.70% | 4.30% | 6.98% | 4.00% | 4.28% |
| | RRT 1.05 | 0.16% | — | 0.08% | 0.05% | 0.06% |
| | RRT 1.08 | 0.13% | 0.11% | 0.10% | 0.08% | 0.05% |
| | RRT 1.13 | 0.05% | 0.03% | 0.04% | 0.06% | 0.09% |
| | RRT 1.17 | 0.05% | 0.03% | 0.03% | 0.06% | 0.04% |
| | RRT 1.19 | 0.06% | 0.06% | 0.06% | 0.05% | 0.05% |
| | RRT 1.21 | 0.04% | — | 0.02% | — | — |
| | RRT 1.23 | 0.18% | 0.08% | 0.12% | 0.11% | 0.14% |
| | RRT 1.25 | 1.24% | 0.34% | 0.73% | 0.18% | 0.20% |
| | RRT 1.27 | 0.02% | 0.02% | 0.02% | 0.02% | 0.03% |
| | RRT 1.30 | 0.05% | 0.05% | 0.05% | 0.06% | 0.05% |
| | RRT 1.38 | 0.09% | 0.13% | 0.12% | 0.16% | 0.15% |
| | RRT 1.40 | — | — | — | 0.02% | 0.02% |
| Total Impurities | | 36.48% | 15.86% | 24.49% | 14.40% | 15.39% |

Thus, from "time-zero" of the stability testing, a substantial number of related substances (impurities and degradation products) were identified. By Day 7, the assay number decreased, indicating degradation of the BBI-4000 and some degradation products were noticeably increased (RRT 0.84 and RRT 0.80), indicating lack of stability of this formulation system. Adjustment of pH, by itself, although providing a lower percent degradation in the buffered formulation, did not resolve the issue.

A second experiment was conducted using a preparation comprising 2% of a soft glycopyrrrolate ester (SGE) in an aqueous buffer system, which was tested for stability at refrigerated, 25° C. (RT), and 40° C., for 7 days, and showed the same trend or similar results.

Thus, independent of pH, when water or aqueous buffer is present, the SGE is relatively rapidly degraded and is substantially reduced in less than one week.

Example 2—Anhydrous Formulations

For preparing an anhydrous formulation, it is noted that no water or aqueous solution is added to the preparation. Because the raw materials, excipients, and the like are not dried or subjected to any drying process, some water, as residual moisture, may be present.

The anhydrous formulations are based on: ethanol (solvent), hexylene glycol (moisturizer), and hydroxypropyl cellulose (HPC, gelling agent), in varying amounts or ratios. Each formulation was given an identification number as follows:
69-1=without antioxidant
73-2=without antioxidant but with polysorbate 80
72-2=adding propylene glycol and polysorbate 80
78-1 and 78-2=different quantities of HPC
79-1=with ascorbic acid as antioxidant/acidifying agent
79-2=with Vitamin E as antioxidant
84-1=with citric acid as antioxidant/acidifying agent
The formulation 84-1 having the formulation shown in Table III: showed good stability and was tested in vivo.

TABLE III

| Component | A 84-1 % (w/w) |
|---|---|
| BB1-4000 | 10 |
| Klucel MF | 1.25 |
| Hexylene Glycol | 10 |
| Dimethiconol Blend 20 | 2.5 |
| Citric Acid, Anh. | 0.1 |
| Ethanol (200 proof) | 76.15 |

Repeat-Dose Studies Up to 14 Days

A 14-Day dermal and systemic toxicity and toxicokinetics study in Gottingen Minipigs was conducted and completed using a formulation based on Formulations 79-1 and 84-1, above, but having a relatively high concentration of the active drug for testing tolerability. Specifically, the composition of the preparation used in this study included BBI-4000 as active ingredient (except in the vehicle-only control), hydroxypropyl cellulose as a gelling agent, hexylene glycol as an emollient, ascorbic acid or citric acid as antioxidant/pH adjustment and ethanol as the anhydrous vehicle.

Three groups of one male and one female animal were included in the main study, Group 1 receiving vehicle, Group 2 receiving BBI-4000 gel at 10% concentration and Group 3 receiving BBI-4000 gel at 20% concentration. All groups received 2 mL of gel formulation, once a day, for 14 consecutive days, applied to approximately 10% of their body surface area on their back.

The study included daily observations of the site of application and scoring of erythema and edema (if present), daily general examinations including heart rate as well a pupil size assessments at days 1, 2, 3, 5, 7, 10 and 14. The frequent observations of heart rate and pupil size were intended to identify any potential systemic anticholinergic effect. Main organs were evaluated during necropsy and histopathology evaluation was completed for treated and untreated skin. Blood samples for chemistry and hematology analysis were collected as well as PK samples.

The results indicated that the composition was well-tolerated, there was no evidence of erythema or edema in the treated skin of any of the animals. Daily observation did not report any abnormality in heart rate or any other parameter. Pupil size assessments were reported as normal at all times in all animals. Blood chemistry and hematology parameters were reported within normal ranges. The necropsy did not reveal any abnormalities in any of the animals.

Histopathology analysis for the skin treated with an anhydrous composition comprising BBI-4000 was unremarkable and identical to non-treated and vehicle treated skin. All skin samples from the different groups were similar with minor nonspecific changes that do not appear to be related to treatment. Mild, superficial inflammation reported in the dermis of most skin samples from all groups and from the non-treated areas, suggests this finding is not drug or composition related, but associated with the caging of the animals.

The estimated BBI-4000 dose applied to the skin in this study was 40 mg/kg/day for Group 3 and 20 mg/kg/day for Group 2.

The PK analysis revealed variable, dose related systemic exposure of BBI-4000. The highest concentration was observed at 2 hours after Day-14 dosing in a minipig receiving the 20% BBI-4000 concentration. Most of the PK values for the carboxylic acid metabolite were below the lowest limit of quantification (LLOQ=4.75 ng/mL for this assay), consistent with the short half-life of this metabolite. Group 1 (vehicle) did not report any value above the LLOQ, as expected.

It was noted during the study that a reddish formulation residue was observed in the skin of all animals receiving the ascorbic-acid-containing formulation. Although the residue could be removed with wiping from the skin, this type of residue would not be acceptable to a human subject; therefore, additional formulations were evaluated. A new experiment was conducted in 2 new pigs with a new formulation removing the ascorbic acid, adding citric acid and dimethiconol blend 20. Testing of the citric acid-containing formulation was also well tolerated and no reddish or pink-colored residue was observed.

The following formulations, shown in Table IV, were tested for stability:

TABLE IV

| Component | A 84-1 % (w/w) | B 84-2 % (w/w) | C 84-3 % (w/w) |
|---|---|---|---|
| BBI-4000 | 10 | 10 | 10 |
| Klucel MF | 1.25 | 1.25 | 1.25 |
| Hexylene Glycol | 10 | 10 | 10 |
| Dimethiconol Blend 20 | 2.5 | 2.5 | 2.5 |
| BHT | — | 0.1 | — |
| Propyl Gallate | — | — | 0.05 |
| Citric Acid, Anh. | 0.1 | 0.1 | 0.1 |
| Ethanol (200 proof) | 76.15 | 76.05 | 76.1 |

Impurity levels determined at time "zero" are shown in Table V, below:

TABLE V

| | | BB-84-1 | | 88-84-2 | | | BB-84-3 | |
|---|---|---|---|---|---|---|---|---|
| BBI-4000 | Assay (Wt %) | 9.81% | | 9.89% | | | 9.72% | |
| | TAN % | 98.19 | | 95.15% | | | 92.17% | |
| | | RRT | Area % | RRT | Area % | Area | RRT | Area % | Area |
| Impurities | | RRT 0.80 | 0.67% | | | | | | |
| | | RRT 0.96 | 0.10% | RRT 0.80 | 0.62% | | RRT 0.64 | 6.07% | 39617.03 |
| | | RRT 1.09 | 0.86% | RRT 0.96 | 0.07% | | RRT 0.80 | 0.69% | |
| | | RRT 1.48 | 0.19% | RRT 1.09 | 0.79% | | RRT 0.96 | 0.09% | |
| | | | | RRT 1.49 | 0.16% | | RRT 1.09 | 0.81% | |
| | | | | RRT 2.05 | 0.90% | 39245.56 | RRT 1.49 | 0.17% | |
| | | | | RRT 2.07 | 2.31% | | | | |
| | | | | 100774.43 | | | | | |
| Total Impurities | | 1.82% | | 4.85% | | | 7.83% | |

Impurity levels determined at 7 days, under accelerated conditions, 40° C., are shown in Table VI, below:

TABLE VI

| | | BB-84-1 | | BB-84-2 | | | BB-84-3 | |
|---|---|---|---|---|---|---|---|---|
| BBI-4000 | Assay (Wt %) | 10.32% | | 10.18% | | | 10.08% | |
| | TAN % | 97.89% | | 94.75% | | | 93.84% | |
| | | RRT | Area % | RRT | Area % | Area | RRT | Area % | Area |
| Impurities | | RRT 0.80 | 0.59% | RRT 0.80 | 0.42% | | | | |
| | | RRT 0.82 | 0.03% | RRT 0.91 | 0.16% | | RRT 0.64 | 4.28% | |
| | | RRT 0.91 | 0.17% | RRT 0.96 | 0.15% | | | | 212713.37 |
| | | RRT 0.96 | 0.29% | RRT 1.09 | 0.96% | | RRT 0.80 | 0.58% | |
| | | RRT 1.08 | 0.04% | RRT 1.49 | 0.18% | | RRT 0.96 | 0.20% | |
| | | RRT 1.09 | 0.80% | RRT 1.50 | 0.02% | | RRT 1.09 | 0.90% | |

TABLE VI-continued

|  | Day 7 Results | | | | | |
|---|---|---|---|---|---|---|
|  | RRT 1.49 | 0.19% | RRT 2.05 | 0.88% | 44108.37 RRT 1.49 | 0.18% |
|  | RRT 1.50 | 0.01% | RRT 2.07 | 2.49% | 125413.63 RRT 1.50 | 0.02% |
| Total Impurities |  | 2.11% |  | 5.25% |  | 6.16% |

All formulations showed good stability, however fewer impurities were identified in formulations where antioxidants propyl gallate or BTH were absent from the formulation.

Further stability testing has been completed for a 3-month time-frame, using Formulation No. 84-1, tested at three temperatures: accelerated (40° C.), room temperature (25° C.), and refrigerated (about 4° C.). Formulation No. 84-1 was specifically prepared using the following preparation instructions:
  a) Combine the hexylene glycol and ethanol in a suitable container and mix.
  b) Add the citric acid and stir to dissolve.
  c) Add the active (BBI-4000) and stir to dissolve.
  d) Add the Klucel MF and stir to dissolve, to increase viscosity of the product.
  e) Lastly, add the Dimethiconol Blend 20 and briefly disperse.
  f) Homogenize the mixture of steps a) through e). For small batches, homogenation can be carried out by passing/mixing between 2 syringes connected with a micro-emulsifying needle. For larger batches, an overhead or inline homogenizer may be required.

The results of the 3-month stability study are provided in Table VII, below:

TABLE VII

|  | Day | | | | | | | |
|---|---|---|---|---|---|---|---|---|
|  | 0 | 7 D-40 C. | 14 D-40 C. | 30 D-40 C. | 30 D-5 C. | 90 D-5 C. | 30 D-25 C. | 90 D-25 C. |
| Assay | 9.81 | 10.32 | 10.21 | 10.25 | 9.32 | 10.50 | 10.26 | 10.63 |
| Total Impurities | 1.82 | 2.12 | 2.12 | 3.48 | 2.77 | 2.35 | 3.29 | 3.87 |

Example 3—Clinical Study

A clinical study to test this formulation is planned, and may include the following:
The objectives of this study are to:
Assess the safety of BBI-4000 in subjects with hyperhidrosis, and
Evaluate the treatment effect in gravimetrically assessed sweat production and Hyperhidrosis Disease Severity Scale (HDSS) of BBI-4000 when applied topically in subjects with axillary hyperhidrosis.

To be conducted is a single-center, randomized, double blind, vehicle-controlled, split-body study in subjects with axillary hyperhidrosis. The study will consist of up to 2 consecutive cohorts, as follows:
Cohort 1 will compare BBI-4000 5% gel versus vehicle in 6-12 subjects following a split-body design (i.e. one axilla will receive BBI-4000 5% gel and the other will receive vehicle);
Cohort 2 will be initiated after ensuring good tolerability and no significant dose limiting adverse events from cohort 1 and will compare BBI-4000 10% gel versus, BBI-4000 5% gel versus vehicle in 18 subjects following a parallel design.

In all cohorts, study medication will be applied once a day for 14 consecutive days. Visits for each cohort will be scheduled at screening (day −3 to −7) baseline (Day 1), Day 3, Day 8, Day 15 and Day 16.

Subjects must fulfill all of the following criteria to be eligible for study admission:
Male or Female subjects from 18 to 45 years of age in good general health.
Diagnosis of primary axillary hyperhidrosis that meets the following criteria: HDSS score of 3 or 4
Gravimetric test at baseline indicating at least 50 mg of sweat production at rest by each axilla, in 5 min (room temperature, 25° C.)
Bilateral and Symmetrical
At least 6 months duration
The ability to understand and sign a written informed consent form, which must be obtained prior to treatment.
The ability to understand and sign a Health Insurance Portability and Accountability Act (HIPAA) authorization form which shall permit the use and disclosure of the subject's individually identifiable health information.
The ability to understand and follow all study related procedures including study drug administration.

A composition comprising BBI-4000 or comprising vehicle only will be applied once daily in the evening (immediately before bed-time). Subjects will apply 0.5 mL of the corresponding study product covering the entire axilla, as per randomization schedule. Subjects should not shower, bathe, or apply any other product in the axillary area within 6 hours of study drug administration.

Efficacy will be assessed measuring the change in gravimetrically measure sweat production from baseline to end of treatment and change in HDSS from baseline to end of treatment. Local tolerability assessments (scaling, dryness, erythema, burning, and itching) will also be carried out.

While certain preferred and alternative embodiments of the invention have been set forth for purposes of disclosing the invention, modifications to the disclosed embodiments may occur to those who are skilled in the art. Accordingly, this specification is intended to cover all embodiments of the invention and modifications thereof which do not depart from the spirit and scope of the invention.

What is claimed is:
1. A method of treating hyperhidrosis in a subject, said method comprising topically administering an anhydrous topical gel composition to skin of an area of a subject suffering from hyperhidrosis, before bedtime, such that, compared to untreated, baseline conditions, sweat produc- tion is reduced by at least 25% for at least six (6) hours; and such that sweat production is reduced by an amount substantially equivalent to an amount that sweat production is reduced as compared to untreated, baseline conditions, following administration of a composition comprising the same concentration of glycopyrrolate, and with an improved safety profile compared to topical glycopyrrolate, wherein said anhydrous topical gel composition comprises the following ingredients:

(a) a compound having the formula:

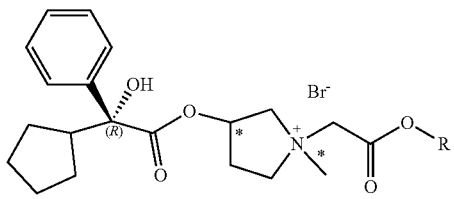

wherein R is methyl or ethyl, said compound having the R stereoisomeric configuration at the 2 position and the R, S or RS stereoisomeric configuration at the 1' and 3' positions, or being a mixture thereof;

(b) anhydrous ethanol present in an amount sufficient to act as a non-aqueous solvent for the compound of formula (2);

(c) optionally, at least one gelling or viscosity-controlling ingredient; and (d) optionally, at least one additional carrier or excipient;

provided that said anhydrous topical gel composition comprises from about 1% to about 20% w/w of the compound of formula (2), wherein the gelling or viscosity-controlling ingredient comprises hydroxypropyl cellulose, and wherein the anhydrous topical gel composition further comprises citric acid and hexylene glycol.

2. The method of claim 1, said anhydrous topical gel composition comprises at least about 70% w/w anhydrous ethanol.

3. The method of claim 1, said anhydrous topical gel composition comprises from about 70% to about 99.99% w/w anhydrous ethanol.

4. The method of claim 1, wherein said anhydrous topical gel composition comprises at least one additional carrier or excipient.

5. The method of claim 1, wherein the compound of formula (2) is selected from the group consisting of:

(a) (2R,3'R) 3-(2-cyclopentyl-2-phenyl-2-hydroxyacetoxy)-1-(ethoxycarbonylmethyl)-1-methylpyrrolidinium bromide;

(b) (2R,3'S) 3-(2-cyclopentyl-2-phenyl-2-hydroxyacetoxy)-1-(ethoxycarbonylmethyl)-1-methylpyrrolidinium bromide;

(c) (2R,1'R,3'S) 3-(2-cyclopentyl-2-phenyl-2-hydroxyacetoxy)-1-(ethoxycarbonylmethyl)-1-methylpyrrolidinium bromide;

(d) (2R,1'S,3'S) 3-(2-cyclopentyl-2-phenyl-2-hydroxyacetoxy)-1-(ethoxycarbonylmethyl)-1-methylpyrrolidinium bromide;

(e) (2R,1'R,3'R) 3-(2-cyclopentyl-2-phenyl-2-hydroxyacetoxy)-1-(ethoxycarbonylmethyl)-1-methylpyrrolidinium bromide;

(f) (2R,1'S,3' R) 3-(2-cyclopentyl-2-phenyl-2-hydroxyacetoxy)-1-(ethoxycarbonylmethyl)-1-methylpyrrolidinium bromide;

(g) (2R,3'R) 3-(2-cyclopentyl-2-phenyl-2-hydroxyacetoxy)-1-methyl-1-methoxycarbonylmethylpyrrolidinium bromide;

(h) (2R,3'S) 3-(2-cyclopentyl-2-phenyl-2-hydroxyacetoxy)-1-methyl-1-methoxycarbonylmethylpyrrolidinium bromide;

(i) (2R,1'R,3'R) 3-(2-cyclopentyl-2-phenyl-2-hydroxyacetoxy)-1-methyl-1-methoxycarbonylmethylpyrrolidinium bromide;

(j) (2R,1'R,3'S) 3-(2-cyclopentyl-2-phenyl-2-hydroxyacetoxy)-1-methyl-1-methoxycarbonylmethylpyrrolidinium bromide;

(k) (2R,1'S,3'R) 3-(2-cyclopentyl-2-phenyl-2-hydroxyacetoxy)-1-methyl-1-methoxycarbonylmethylpyrrolidinium bromide; and (l) (2R,1'S,3'S) 3-(2-cyclopentyl-2-phenyl-2-hydroxyacetoxy)-1-methyl-1-methoxycarbonylmethylpyrrolidinium bromide.

6. The method of claim 1, wherein the compound of formula (2) is at a concentration of from about 2% w/w to about 10% w/w of the anhydrous topical gel composition.

7. The method of claim 1, wherein said anhydrous topical gel composition is packaged into a multiple dose container that meters a dose of from about 0.5 ml to about 1.0 ml of the anhydrous topical gel composition for each application.

8. The method of claim 1, wherein said anhydrous topical gel composition is packaged into a single or unit dose container that delivers a single or unit dose of about 0.5 ml to about 1.0 ml of the anhydrous topical gel composition for each application.

9. The method of claim 1, wherein the compound of formula (2) is (2R,3'R) 3-(2-cyclopentyl-2-phenyl-2-hydroxyacetoxy)-1-(ethoxycarbonylmethyl)-1-methylpyrrolidinium bromide.

10. The method of claim 1, wherein the anhydrous topical gel composition further comprises a 6% silicone gum blend in dimethicone.

11. A method of treating hyperhidrosis in a subject, said method comprising topically administering an anhydrous topical gel composition to skin of an area of a subject suffering from hyperhidrosis, such that, compared to untreated, baseline conditions, sweat production is reduced by at least 25% for at least six (6) hours; and such that sweat production is reduced by an amount substantially equivalent to an amount that sweat production is reduced as compared to untreated, baseline conditions, following administration of a composition comprising the same concentration of glycopyrrolate, and with an improved safety profile compared to topical glycopyrrolate, wherein said anhydrous topical gel composition comprises the following ingredients:

(a) a compound having the formula:

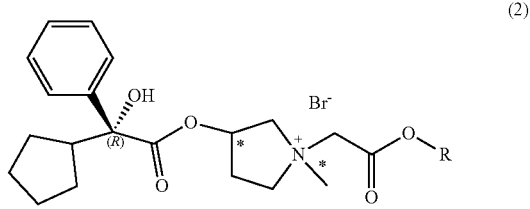

wherein R is methyl or ethyl, said compound having the R stereoisomeric configuration at the 2 position and the R, S or RS stereoisomeric configuration at the 1' and 3' positions, or being a mixture thereof;

(b) anhydrous ethanol present in an amount sufficient to act as a non-aqueous solvent for the compound of formula (2);

(c) at least one gelling or viscosity-controlling ingredient; and (d) optionally, at least one additional carrier or excipient; provided that said anhydrous topical gel composition comprises from about 1% to about 20% w/w of the compound of formula (2), wherein the gelling or viscosity-controlling ingredient comprises hydroxypropyl cellulose, and wherein the anhydrous topical gel composition further comprises citric acid and hexylene glycol.

12. The method of claim 11, said anhydrous topical gel composition comprises comprising at least about 70% w/w anhydrous ethanol.

13. The method of claim 11, said anhydrous topical gel composition comprises comprising from about 70% to about 99.99% w/w anhydrous ethanol.

14. The method of claim 11, wherein said anhydrous topical gel composition comprises at least one additional carrier or excipient.

15. The method of claim 11, wherein the compound of formula (2) is selected from the group consisting of:

(a) (2R,3' R) 3-(2-cyclopentyl-2-phenyl-2-hydroxyacetoxy)-1-(ethoxycarbonylmethyl)-1-methylpyrrolidinium bromide;

(b) (2R,3'S) 3-(2-cyclopentyl-2-phenyl-2-hydroxyacetoxy)-1-(ethoxycarbonylmethyl)-1-methylpyrrolidinium bromide;

(c) (2R,1'R,3'S) 3-(2-cyclopentyl-2-phenyl-2-hydroxyacetoxy)-1-(ethoxycarbonylmethyl)-1-methylpyrrolidinium bromide;

(d) (2R,1'S,3'S) 3-(2-cyclopentyl-2-phenyl-2-hydroxyacetoxy)-1-(ethoxycarbonylmethyl)-1-methylpyrrolidinium bromide;

(e) (2R,1'R,3'R) 3-(2-cyclopentyl-2-phenyl-2-hydroxyacetoxy)-1-(ethoxycarbonylmethyl)-1-methylpyrrolidinium bromide;

(f) (2R,1'S,3' R) 3-(2-cyclopentyl-2-phenyl-2-hydroxyacetoxy)-1-(ethoxycarbonylmethyl)-1-methylpyrrolidinium bromide;

(g) (2R,3'R) 3-(2-cyclopentyl-2-phenyl-2-hydroxyacetoxy)-1-methyl-1-methoxycarbonylmethylpyrrolidinium bromide;

(h) (2R,3'S) 3-(2-cyclopentyl-2-phenyl-2-hydroxyacetoxy)-1-methyl-1-methoxycarbonylmethylpyrrolidinium bromide;

(i) (2R,1'R,3'R) 3-(2-cyclopentyl-2-phenyl-2-hydroxyacetoxy)-1-methyl-1-methoxycarbonylmethylpyrrolidinium bromide;

(j) (2R,1'R,3'S) 3-(2-cyclopentyl-2-phenyl-2-hydroxyacetoxy)-1-methyl-1-methoxycarbonylmethylpyrrolidinium bromide;

(k) (2R,1'S,3' R) 3-(2-cyclopentyl-2-phenyl-2-hydroxyacetoxy)-1-methyl-1-methoxycarbonylmethylpyrrolidinium bromide; and (l) (2R,1'S,3'S) 3-(2-cyclopentyl-2-phenyl-2-hydroxyacetoxy)-1-methyl-1-methoxycarbonylmethylpyrrolidinium bromide.

16. The method of claim 11, wherein the compound of formula (2) is at a concentration of from about 2% w/w to about 10% w/w of the anhydrous topical gel composition.

17. The method of claim 11, wherein said anhydrous topical gel composition is packaged into a multiple dose container that meters a dose of from about 0.5 ml to about 1.0 ml of the anhydrous topical gel composition for each application.

18. The method of claim 11, wherein said anhydrous topical gel composition is packaged into a single or unit dose container that delivers a single or unit dose of about 0.5 ml to about 1.0 ml of the anhydrous topical gel composition for each application.

19. The method of claim 11, wherein the compound of formula (2) is (2R,3'R) 3-(2-cyclopentyl-2-phenyl-2-hydroxyacetoxy)-1-(ethoxycarbonylmethyl)-1-methylpyrrolidinium bromide.

20. The method of claim 11, wherein the anhydrous topical gel composition further comprises a 6% silicone gum blend in dimethicone.

* * * * *